United States Patent [19]

Coste et al.

[11] Patent Number: 5,293,703

[45] Date of Patent: Mar. 15, 1994

[54] FRAME WITH FLEXIBLE TENSIONING STRIPS FOR STRETCHING A MEMBRANE AND GEL

[75] Inventors: Jérome C. D. Coste, Nice; Salah Aksas, Paris; Frédéric Ginot, Versailles; Daniel Cohen, Saint Mande, all of France

[73] Assignee: Bertin & Cie, Plaisir, France

[21] Appl. No.: 910,252

[22] PCT Filed: Dec. 3, 1991

[86] PCT No.: PCT/FR91/00957

§ 371 Date: Jul. 17, 1992

§ 102(e) Date: Jul. 17, 1992

[87] PCT Pub. No.: WO92/10272

PCT Pub. Date: May 25, 1992

[30] Foreign Application Priority Data

Dec. 10, 1990 [FR] France ............................ 90 15409

[51] Int. Cl.⁵ .................. D06C 3/08; B01D 57/02; G01N 27/26
[52] U.S. Cl. ................. 38/102.4; 38/102.91; 204/180.1
[58] Field of Search ........... 204/182.8, 299 R, 180.1, 204/301, 182.9, 182.7; 38/102, 102.1, 102.3, 102.4, 102.5, 102.7, 102.9, 102.91; 101/127.1; 69/46; 34/151, 158; 160/372, 374, 378, 379; 223/61

[56] References Cited

U.S. PATENT DOCUMENTS

| 283,994 | 8/1983 | French | 38/102.4 |
|---|---|---|---|
| 373,027 | 11/1987 | Mullins | 38/102.4 |
| 532,334 | 1/1895 | O'Keeffe | 38/102.4 |
| 801,077 | 10/1905 | Girard | 38/102.4 |
| 1,325,519 | 12/1919 | Jenkins | 38/102.1 |
| 3,523,863 | 8/1970 | Juhos | 168/249 |
| 3,774,326 | 11/1973 | Selden | 38/102.4 |
| 3,979,846 | 9/1976 | Euzarraga | 38/102.5 X |
| 4,860,467 | 8/1989 | Larson | 38/102.4 |
| 4,883,597 | 11/1989 | Perlman | 210/640 |

FOREIGN PATENT DOCUMENTS

| 0309303 | 3/1989 | European Pat. Off. . |
| 0358556A1 | 3/1990 | European Pat. Off. . |
| 3032070 | 7/1982 | Fed. Rep. of Germany . |
| 2389701 | 1/1979 | France .................. 38/102.3 |

*Primary Examiner*—Clifford D. Crowder
*Assistant Examiner*—Ismael Izaguirre
*Attorney, Agent, or Firm*—Watson, Cole, Grindle & Watson

[57] ABSTRACT

A frame for use in making a membrane lined with a gel layer includes two spaced apart bars to which opposite edges of a membrane can be connected and which are connected by two pairs of elastic strips. Cam elements are positioned between the strips of each pair of elastic strips to move the strips apart or allow them to come together, thereby causing the bars to move together for attachment of the membrane, or apart to stretch and tension the membrane after a gel has been cast thereon.

9 Claims, 1 Drawing Sheet

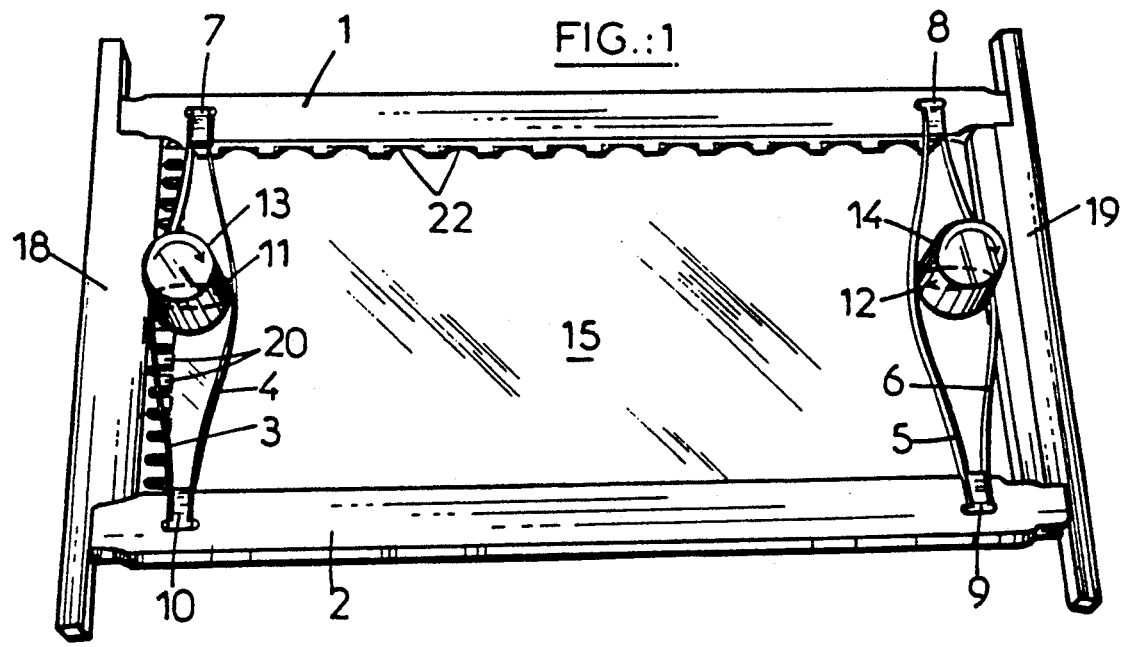
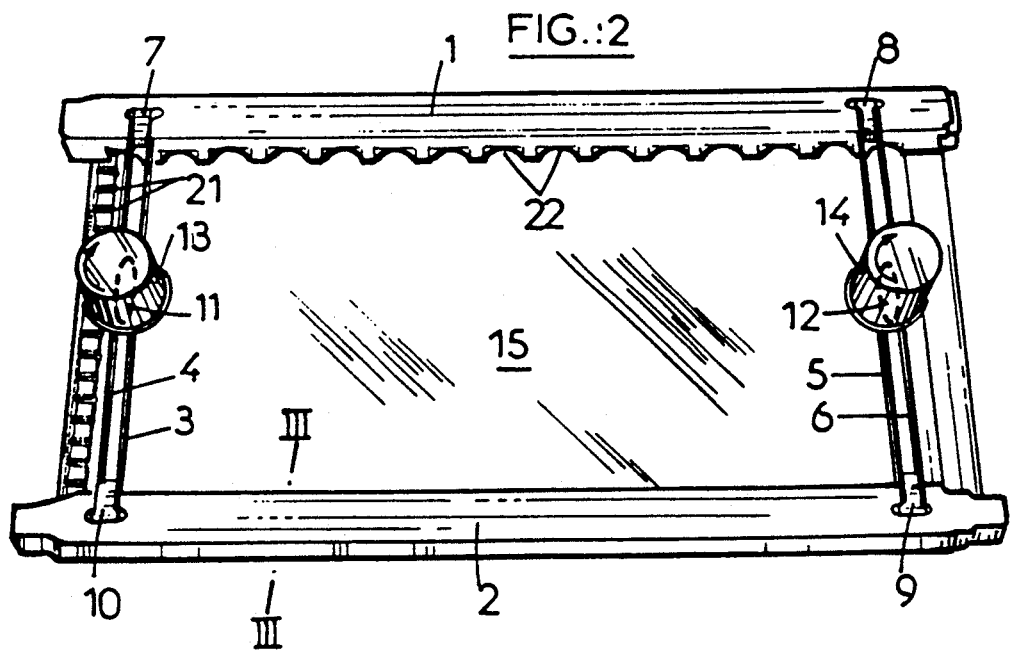
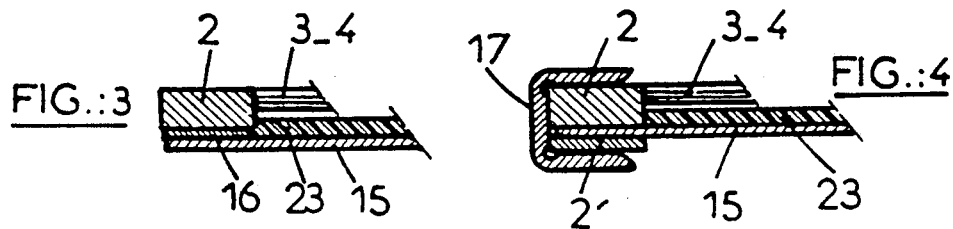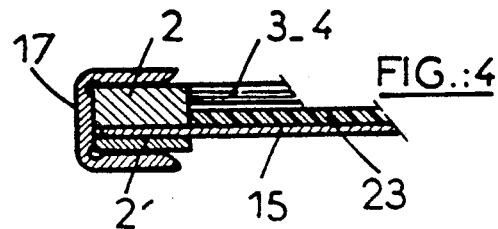

FRAME WITH FLEXIBLE TENSIONING STRIPS FOR STRETCHING A MEMBRANE AND GEL

BACKGROUND OF THE INVENTION

Field of the Invention

The present invention relates to a method for preparing a membrane lined with a layer of a gel and a frame for supporting such a membrane, which frame is designed for the implementation of this method. More particularly, the invention relates to the making up of a gel/membrane assembly which can be used in a technique for separating macromolecules by electrophoresis.

In such a technique a layer of a gel such as agarose or a polyacrylamide and an electric field established between two opposite edges of the layer are used. Samples of macromolecules, for example macromolecules of nucleic acid, to be separated are deposited in wells formed in the gel along one of these two edges of the layer. The assembly is next immersed in a suitable electrophoresis liquid. Under the effect of the electric field, the macromolecules of the samples housed in the wells move towards the opposite edge of the layer, through the gel, at rates which depend notably on their molecular mass, so that at the end of a given time, macromolecules of different molecular masses have traveled different distances into the gel.

The macromolecules thus separated are next transferred, either by fluid entrainment or by means of an electric field applied perpendicular to the gel layer, onto a membrane placed against one face of this layer, with a view to their subsequent hybridization and to their subsequent detection. A method and an electrophoresis device, which are designed for achieving such a controlled migration of macromolecules in a stack of rectangular plates of gel, is described in European Patent Application Publication No. 358,556.

When a membrane is used for supporting the gel layer, the making-up of the gel/membrane assembly is particularly tricky on account of the fineness and of the lack of stiffness of the membrane used, commonly a thin sheet of nitrocellulose, optionally filled with nylon in order to increase its mechanical strength.

Known frames for supporting such a membrane have the drawback of not enabling this membrane to be held in a plane under uniform tension. Pleats resulting from tension defects then form in the membrane. The gel layer which is cast onto a membrane thus pleated has deformations which oppose a steady progression of the macromolecules in the layer and render the result of the migration useless. The elimination of these pleats requires lengthy and fastidious manipulations which are incompatible with the requirements of an automated, or indeed industrial, manufacture.

SUMMARY OF THE INVENTION

The object of the present invention is therefore to provide a method for preparing such a membrane lined with gel and a frame for the implementation of this method, which enable the formation of pleats in the membrane to be prevented.

The object of the present invention is also to provide such a method and such a frame which are compatible with industrial means for making up membranes lined with gel and for manipulating the frames supporting these membranes.

These objects of the invention are achieved, as well as others which will emerge on reading the present description, with a method for preparing a membrane lined with a layer of a gel, according to which the membrane is firstly laid flat in a horizontal plane and a gel is then cast onto this membrane, this method being noteworthy in that the membrane is put under tension by a traction exerted between at least two substantially parallel opposite edges of this membrane.

By virtue of this tensioning of the membrane, pleats are eliminated and the gel spreads out as a layer of uniform thickness over the membrane.

For the implementation of this method, the invention provides a frame for supporting the membrane, which comprises at least two bars and means of attaching a membrane to these bars, along two parallel edges of this membrane. The frame is noteworthy in that it comprises means of causing the relative position of the two bars to be varied progressively between a position where the membrane is unstretched and a position where this membrane is stretched between its two bars.

The means of causing the relative position of the bars to vary comprise at least two identical elastic strips, each secured by its ends in two corresponding ends of the bars which are attached to the membrane, it being possible for these strips to be flexed in order to move the bars closer to each other with a view to attaching the membrane to the bars. The strips are provided to interact with means of controlling their flexure.

According to a preferred embodiment of the frame according to the invention, the frame comprises two pairs of parallel elastic strips, each secured between two corresponding ends of the bars, and means of controlling the flexure of the strips of each pair in order to move them closer or move them apart symmetrically. These means can advantageously be constituted by a rotary cam inserted between the two strips of one pair.

Other characteristics and advantages of the method and of the frame according to the present invention will emerge on reading the description which follows and by examining the attached drawing in which:

BRIEF DESCRIPTION OF THE DRAWINGS

FIG. 1 is a perspective view of the support frame according to the invention, in the configuration which is given to it in order to prepare it for the casting of a gel layer onto a membrane attached to this frame, FIG. 2 is a perspective view of the same frame, in the configuration which it has after the tensioning of the membrane which it carries, in accordance with the teachings of the present invention, FIG. 3 is a partial sectional view of the frame of FIGS. 1 and 2 taken along the line of section III—III of FIG. 2, and FIG. 4 is a sectional view similar to that of FIG. 3 of another embodiment of the frame according to the present invention.

DETAILED DESCRIPTION OF PREFERRED EMBODIMENTS

As FIGS. 1 and 2 of the attached drawing show, the support frame according to the invention comprises two symmetrical bars 1 and 2 which are braced by pairs of elastic strips 3, 4 and 5, 6. These strips have the same length and are secured perpendicularly at 7, 8, 9, 10, in corresponding ends of the two bars 1 and 2, so as to define with these bars a rectangular frame on two opposite edges of which frame these bars are fitted with a pair of parallel strips which are moved away from each other slightly.

These strips are made from a non-metallic non-conducting material which is flexible but not extensible, such as a composite material, for example a pultruded epoxy glass. Thus, if these strips are deformed, as illustrated in FIG. 1, the length of the projection of the strip on an axis perpendicular to the two bars 1, 2 diminishes, which has the effect of moving the bars closer to each other. If the deformations applied to the four bars are identical, the bars furthermore remain parallel to each other.

According to the invention, this mechanical structure is used in order to stretch a membrane which is to receive a layer of a gel. In order to do this, a rectangular portion of this membrane is attached beneath the frame of FIGS. 1 and 2, whereas means 11, 12 for controlling the flexure of the strips are inserted between the strips 3, 4 and 5, 6 respectively. These means 11, 12 can, for example, take the form of wedges or, as shown in FIG. 1, oblong cams integral with knurled cylindrical parts 13, 14 respectively, enabling them to be rotated conveniently between a position where the cam does not load the strips (FIG. 2) and a position where it does load these strips by deforming them (FIG. 1) so as to move the bars 1, 2 closer to each other, in parallel.

According to the invention, a membrane 15 is attached by two opposite edges to the bars 1 and 2 while the frame is in the position shown in FIG. 1. The attachment means used can be an adhesive product, such as a double-sided adhesive tape 16 (see the partial cross section of FIG. 3) which is fixed to the membrane beforehand with a temporary protection. As a variant, the two edges of the membrane 15 can be clamped between a bar 1, 2 and a counter-bar 1', 2' (see the partial cross section of FIG. 4), a U-shaped clipping profile 17 being passed over the assembly in order to press these two elements towards each other.

After the attachment of a membrane 15 to the frame (1, 2, 3, 4, 5, 6), the method for preparing a membrane lined with a gel layer according to the invention is carried out in the following manner.

The frame carrying the unstretched membrane is laid down on a perfectly flat and horizontal support against which the membrane is applied. The horizontality is checked with a water level. Additional bars 18, 19 are mounted on the frame in the vicinity of the elastic strips, so as to delimit on the subjacent membrane, with the bars 1, 2, a surface which is to receive a gel layer.

It will be noted that one 18 of the bars 18, 19 has, facing the delimited surface, a surface carrying many aligned indentations 20 forming a comb.

A predetermined quantity of a gel which is liquid but which is setting progressively at the ambient temperature, for example, is then cast onto the membrane 15 within the frame according to the invention. This gel then spreads out by gravity over the membrane as a layer 23 of perfectly uniform thickness (see FIGS. 3 and 4).

In order to avoid, in accordance with an essential objective of the invention, the presence of pleats on the membrane, the latter can be stretched just before the casting of the gel, by a rotation of the cams 11, 12 suitable for unstretching the elastic strips 3, 4, 5, 6 (see FIG. 2) and therefore to move the bars 1, 2 away from each other against the resistance of the membrane 15 thus put under tension.

It will be noted that, during the casting of the gel, the latter insinuates between the indentations 20 of the bar 18 which has the effect of forming a row of wells 21 on one edge of the layer, wells which are intended to receive samples of macromolecules to be studied, as indicated in the preamble of the present description, when the intended application is the controlled migration of these macromolecules by electrophoresis.

The bars 18, 19 are detachable and are removed from the frame after the setting of the gel (see FIG. 2). The frame thus barped carries a gel layer whose wells 21 are then clear and ready to receive the macromolecules to be studied.

It will be noted that the bars 1, 2 carry, on their lateral surface on the inside of the frame, rows of rounded teeth 22. This is an arrangement which contributes to the fastening of the gel layer to the bars during the setting of the gel. It will be furthermore noticed, in FIGS. 3 and 4, that the edges of the layer or plate of gel remain in contact with the inner faces of the bars 1 and 2.

The frame thus lined with a membrane carrying a layer of@a suitable gel of calibrated thickness can then be inserted, after filling the wells 21, into a device such as that described in and designed for receiving a plurality of such frames and for ensuring simultaneously in the latter the necessary electrophoretic migrations.

It is now apparent that the method according to the invention does provide the essential advantage indicated, namely the possibility of preparing a gel layer, of a few millimeters thickness for example, on a pleat-free, perfectly stretched membrane.

It is also immediately apparent to the person skilled in the art that the various operations for attaching the membrane to the support frame, for casting the gel and for putting the membrane under tension can be automated without particular difficulties and therefore lend themselves to industrialization of the manufacture of such gel/membrane assemblies. This is one significant advantage of the invention over the current techniques for preparing such assemblies which require both time and skill without always being able to avoid the pitfall of pleat formation. Furthermore, within the framework of an industrial manufacture, it becomes possible to control the tension of the membrane which contributes to the reproducibility of the macromolecule migration spectra transferred to the membrane.

It will furthermore be seen that the membrane can be detached from the frame according to the invention, whether this membrane is attached to this frame by the means illustrated in FIG. 3 or in FIG. 4. The frame can then be used again, which further lowers the cost of the preparation method according to the invention, especially within the framework of industrialization of this method.

Of course the invention is not limited to the embodiment described and shown, which has been given by way of example only. Thus, the frame described is braced by two pairs of elastic strips 3, 4 and 5, 6. It would be possible to design a frame comprising a single elastic strip there where there are two of them in the embodiment described. However, the use of pairs of parallel and embedded strips which are moved apart is advantageous in that each pair itself constitutes a rectangle which deforms symmetrically easily but which can be deformed asymmetrically with difficulty, which opposes any deformation of the frame in its plane and which furthermore opposes any buckling of this frame by virtue of the fact that the strips are arranged in planes perpendicular to the plane of the frame.

It will also be seen that the means used according to the invention f or stretching a membrane between two of its edges could be duplicated between the two other edges in order to put the membrane into bi-directional tension, which is even more suitable, in principle, for promoting the perfect planarity of the membrane. The membrane could also be stretched in a direction parallel to the direction of migration of the macromolecules rather than in a direction perpendicular to the latter direction.

We claim:

1. A frame for supporting and stretching a membrane, comprising at least two parallel bars and means for attaching the membrane to said bars along two parallel edges of said membrane, and means for causing the relative positioning of the two bars to vary between a position where said membrane is unstretched and a position where said membrane is stretched between said bars, said means for causing the relative positioning of said bars to vary comprising two pairs of closely spaced parallel and identical elastic strips having tow ends, each strip being secured by its respective ends to two corresponding ends of said bars, said strips being flexed apart from each other in order to move the bars closer to each other for attaching the membrane to the bars.

2. The frame as claimed in claim 1, wherein the membrane supports a layer of a gel which is cast onto the membrane while the latter is supported horizontally by the bars in the closer-together position.

3. The frame as claimed in claim 2, including means for controlling the flexure of the elastic strips.

4. The frame as claimed in claim 2, comprising two pairs of parallel elastic strips, each secured between two corresponding ends of the bars, the means of controlling the flexure of the strips of each pair being constituted by a rotary cam inserted between two strips of one pair.

5. The frame as claimed in claim 1, comprising two additional bars sized in order to be installed between the two bars supporting the membrane so as to delimit with these membrane-supporting bars, on the membrane, a surface over which the gel to be cast onto the membrane has to be retained until gel setting.

6. The frame as claimed in claim 5, wherein at least one of the additional bars is detachable and has indentations defining wells on one edge of the surface of the membrane reserved for the casting of the gel.

7. The frame as claimed in claim 3, wherein the bars supporting the parallel edges of the membrane comprise teeth on their surfaces for containing the gel on the surface of the membrane.

8. The frame as claimed in claim 1, wherein the membrane is attached to the support bars by a double-sided adhesive tape.

9. The frame as claimed in claim 1, comprising gripping means for attaching the membrane to each support bar, the membrane being attached between one surface of one bar and one surface of a corresponding counter-bar, said means gripping the bar and the counter-bar.

* * * * *

UNITED STATES PATENT AND TRADEMARK OFFICE
CERTIFICATE OF CORRECTION

PATENT NO. : 5,293,703
DATED : March 15, 1994
INVENTOR(S) : Jerome C.D. Coste, et al It is certified that error appears in the above-indentified patent and that said Letters Patent is hereby corrected as shown below:

Column 5, line 25, change "tow" to --two--.

Signed and Sealed this

Sixteenth Day of August, 1994

Attest:

BRUCE LEHMAN

Attesting Officer     Commissioner of Patents and Trademarks